United States Patent [19]

Brewster

[11] Patent Number: 5,922,309

[45] Date of Patent: Jul. 13, 1999

[54] NON-WHITENING UNDERARM COMPOSITIONS

[75] Inventor: David Allen Brewster, Shelton, Conn.

[73] Assignee: Cheesebrough-Pond's USA Co., Greenwich, Conn.

[21] Appl. No.: 08/997,679

[22] Filed: Dec. 23, 1997

[51] Int. Cl.$^6$ ................................ A61K 7/32; A61K 7/00
[52] U.S. Cl. ............................. 424/65; 424/400; 424/401
[58] Field of Search ................................ 424/65, 400, 401

[56] References Cited

U.S. PATENT DOCUMENTS

| | | | |
|---|---|---|---|
| 5,449,511 | 9/1995 | Coe | 424/65 |
| 5,534,246 | 7/1996 | Herb et al. | 424/66 |

*Primary Examiner*—Shelley A. Dodson
*Attorney, Agent, or Firm*—Milton L. Honig

[57] ABSTRACT

An underarm treatment composition is provided including a deodorant and/or antiperspirant active and cyclomethicone in hexameric form. No more than 35% of the composition includes cyclomethicone in tetrameric or pentameric form. The compositions are non-whitening when applied onto the skin.

9 Claims, No Drawings

NON-WHITENING UNDERARM COMPOSITIONS

BACKGROUND OF THE INVENTION

1. Field of the Invention

The invention relates to non-whitening underarm compositions having perspiration inhibiting properties and/or deodorancy.

2. The Related Art

Antiperspirant products frequently result in objectionable aesthetic characteristics including tackiness and whitening. The term whitening refers to the presence of visible residues of white substances remaining on the skin.

U.S. Pat. No. 5,449,511 (Coe) reports an anhydrous antiperspirant product containing a non-volatile water soluble liquid masking agent interactive with the antiperspirant active salt. The interaction is reported to essentially eliminate discernible whitening without substantially diminishing perspiration inhibiting activity. Most preferred as masking agent are alkoxylated alcohols such as PPG-10 butane diol and dimethicone copolyol.

A problem often encountered with masking agents is that they interfere with other physical properties. For instance, solid, gel or cream type products require structurants to impart rigidity. Many masking agents plasticize to increase tackiness and interfere with the structurant effect. Consequently, considerable research has been conducted to discover non-whitening agents which have little or no adverse affect on other physical properties.

Accordingly, it is an object of the present invention to provide an underarm product which after application leaves, for at least 1 hour, preferably 3 hours but optimally 24 hours, transparent (non-white) product residues on the skin.

Another object of the present invention is to provide an underarm product which not only is non-whitening but also has no detrimental effect upon other physical properties of the product.

These and other objects of the present invention will become more readily apparent from consideration of the following summary and detailed description.

SUMMARY OF THE INVENTION

A non-whitening underarm composition is provided including:

(i) an underarm active present in an effective amount to inhibit odor or to reduce perspiration;

(ii) from 5 to 80% by weight of the composition of hexameric cyclomethicone; and (iii) from 0 to 35% by weight based on total cyclomethicone present in the composition of tetrameric and pentameric cyclomethicone.

DETAILED DESCRIPTION OF THE INVENTION

Now it has been found that non-whitening underarm compositions can be achieved through incorporation of a volatile siloxane of predominantly hexameric cyclomethicone. These compositions require restriction on the amounts of tetramer and pentamer. Thus, no more than 35%, preferably no more than 20%, and optimally no more than 10% of these lower molecular weight cyclomethicones, based on total weight cyclomethicone, should be present in the compositions. In terms of weight ratio, the amount of hexameric to combined tetrameric/pentameric cyclomethicone will be at least about 1:1, preferably at least about 2:1.

A first essential element of compositions according to the invention is that of a deodorant and/or antiperspirant active. Most preferable is an astringent salt which combines the properties of deodorancy and antiperspirancy. Suitable astringents may be inorganic or organic salts of aluminum, zirconium, zinc and mixtures thereof. Salts useful as astringents or as components of astringent complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y$—$XH_2O$ where Q is chlorine, bromine or iodine, where x is 2 to 5 and x+y=6 and x and y do not need to be integers; and where X is about 1 to 6.

Zirconium compounds which are useful may be represented by the following general empirical formula: $ZnO(OH)_{2-nz}B_z$ wherein z may vary from about 0.9 to 2 and need not be an integer, n is the valence of B, 2-nz is greater than or equal to 0, and B may be selected from the group consisting of halides, nitrate, sulfamate, sulfate and mixtures thereof. As with the basic aluminum compounds, it will be understood that the aforementioned formula is greatly simplified and is intended to represent and include compounds having coordinated and/or bound water in various quantities, as well as polymers, mixtures and complexes of the above. Zirconium hydroxy salts actually represent a range of compounds having various amounts of the hydroxy group, varying from about 1.1 to only slightly greater than 0 groups per molecule.

Several types of complexes utilizing the above astringent salts are known in the art. For example, U.S. Pat. No. 3,792,068 (Luedders et al.), discloses complexes of aluminum, zirconium and amino acids such as glycine. Complexes reported therein and similar structures are commonly known as ZAG. The ZAG complexes ordinarily have an Al:Zr ratio of from about 1.67 to 12.5 and a Metal:Cl ratio of from about 0.73 to 1.93. A preferred aluminum compound for preparation of ZAG type complexes is aluminum chlorhydroxide of the empirical formula $Al_2(OH)_5Cl.2H_2O$. Preferred zirconium compounds for preparation of ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from 1.5 to 1.87 and n is from about 1 to 7. The preferred amino acid for preparing such ZAG-type complexes is glycine of the formula $CH_2(NH_2)COOH$. Spherical ZAG, with particle size 1 to 100 microns, is especially preferred.

More specifically, the following is a list antiperspirant actives useful for the present invention which have approved in listings under the United States Food & Drug Administration, Federal Register. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY and aluminum zirconium trichlorohydrate GLY.

Amounts of the deodorant/antiperspirant active may range from 0.1 to 70%. When the active is an astringent salt, the amounts may range from 1% to 70%, preferably from 15% to 60% by weight calculated on an anhydrous metal salt basis (exclusive of glycine, the salts of glycine or other complexing agents).

Deodorant actives according to the present invention also include materials other than those functioning as antiperspirants. Deodorants should be capable of killing or hindering the growth of microorganisms that generate malodor or that promote the decomposition of body oils into odiferous fatty acids. Most prominent among organic antimicrobial materials are triclosan, triclorban, chlorhexedine and certain fragrant oils known as deo perfumes (e.g. U.S. Pat. No. 4,278,658 to Hooper et al.). Amounts of the organic antimicrobial materials may range from 0.01 to 1%, preferably 0.1 to 0.5% by weight. Inorganic antimicrobial materials may also serve as deodorant actives. These include zinc oxide, zinc hydroxide, zinc carbonate, zinc phenolsulfonate, magnesium oxide, magnesium hydroxide, magnesium carbonate, lanthanum oxide, lanthanum hydroxide, lanthanum carbonate, sodium bicarbonate, potassium bicarbonate and combinations thereof. Amounts of the inorganic materials may range from 0.1 to 60% by weight.

A second essential element to be incorporated into the compositions of this invention is that of a volatile siloxane which is a cyclomethicone hexamer. This material may be present in amounts from 5 to 80%, preferably from 15 to 60%, optimally from 30 to 50% by weight. The hexamer will have the structure:

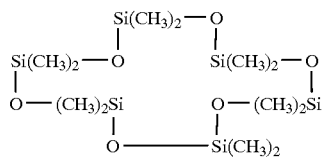

Compositions of the present invention preferably will not contain any low molecular weight cyclomethicones. For instance, levels of tetrameric and pentameric cyclomethicone together will be no higher than 35%, preferably no higher than 20% by weight of the total cyclomethicone present in the compositions. Hexameric cyclomethicone is commercially available as DC 246 from the Dow Corning Company.

Compositions of the present invention may also contain a powdered filler. Illustrative of this category are starches, talc, fumed silica (e.g. Cab-O-Sil from the Cabot Corporation), finely divided silica (e.g. sodium silicate), magnesium aluminum silicate, clays and mixtures thereof. Most preferred and effective are corn starch and modified starches, especially aluminum starch octenyl succinate, commercially available from the National Starch & Chemical Company under the trademark Dry Flo®.

Amounts of the powdered filler can range from 1 to 40%, preferably from 10 to 35%, optimally from 15 to 30% by weight.

Organopolysiloxane elastomers may optionally be present. They will have an average number molecular weight in excess of 2,000, preferably in excess of 1,000,000 and optimally will range from 10,000 to 20 million. Particularly preferred are crosslinked non-emulsifying siloxane elastomers. The term "non-emulsifying" defines a siloxane from which polyoxyalkylene units are absent. Advantageously the elastomers are formed from a divinyl monomer reacting with Si—H linkages of a siloxane backbone. Elastomer compositions are commercially available from the General Electric Company under product designation General Electric Silicone 1229 with proposed CTFA name of Cyclomethicone and Vinyl Dimethicone/Methicone Cross Polymer, delivered as 20–35% elastomer in a cyclomethicone carrier. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries ordinarily are further processed by subjecting them to a high pressure (approximately 1,500 to 3,500 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar, 60 rpm, 15 sec.).

Amounts of the elastomer may range from 0.05 to 30%, optimally from 0.5 to 15%, most preferably from 2 to 10% by weight.

Optionally there may also be present $C_{12}$–$C_{40}$ hydrocarbon. Amounts of this material may range from 1 to 40%, preferably from 5 to 25%, optimally from 10 to 20% by weight. The $C_{12}$–$C_{40}$ hydrocarbon when present may have a viscosity from 10 to 5,000 centistokes at 25° C. The hydrocarbon is preferably a $C_{20}$–$C_{40}$ substance that may either be saturated or unsaturated. Examples include dodecane, tridecane, tetradecane, pentadecane, hexadecane, heptadecane, octadecane, nonadecane, ecosane, heneicosane, docosane, tricosane, tetracosane, pentacosane, isomers of these compounds and mixtures thereof. Most preferred is polydecene available from the Ethyl Corporation under the Ethylflo trademark.

Inert organic particulates may also be included in compositions of the present invention. Illustrative of such materials are the polyolefins (such as polyethylene and polypropylene) and nylon. Most preferred are the spherical or non-spherical polyethylene powders. Amounts of these materials may range from 0.1 to 20%, preferably from 1 to 10% by weight.

Waxes may also be incorporated in compositions of the present invention. Animal origin waxes include beeswax, spermaceti, lanolin and shellac wax. Vegetable origin waxes include carnauba, candelilla, bayberry and sugarcane wax. Especially useful is hydrogenated castor wax. Amounts of the wax may range from 0.5 to 30% by weight.

Compositions of this invention may be in stick, gel, cream and aerosol form. Most preferred however is the cream form, especially ultra dry creams. These creams will have a cone penetration value ranging from 2 to 36 mm, preferably from 10 to 25 mm, optimally from 12 to 20 mm as measured in the Standard Test Method for Cone Preparation of Petrolatum (ASTM D 937).

Advantageously, compositions of the present invention may be anhydrous. By the term "anhydrous" is meant an amount of free water ranging from 0 to 5%, preferably no higher than 3% by weight. Water complexed with aluminum salts may also be present but is not included within the term anhydrous.

The following examples will more fully illustrate the embodiments of this invention. All parts, percentages and proportions referred to herein and in the appended claims are by weight of the total composition unless otherwise indicated.

EXAMPLES 1–7

Formulations in the following Table are dry cream compositions falling within the present invention.

TABLE I

| COMPONENT | EXAMPLE (WEIGHT %) | | | | | | |
|---|---|---|---|---|---|---|---|
| | 1 | 2 | 3 | 4 | 5 | 6 | 7 |
| Hexameric Cyclomethicone | 29.7 | 29.7 | 29.7 | 29.7 | 68.0 | 50.0 | 50.0 |
| Crosslinked Elastomer (25% in Hexameric Cyclomethicone) | 13.5 | 13.5 | 13.5 | 13.5 | 6.0 | 2.0 | 1.0 |
| Polydecene 364 | 10.8 | 10.8 | 10.8 | 10.8 | — | 10.8 | 10.8 |
| ZAG | 26.0 | 26.0 | 26.0 | — | 26.0 | 26.0 | 26.0 |
| Triclosan | — | — | — | 0.5 | — | — | — |
| Corn Starch | 20.0 | — | 18.5 | 20.0 | — | 11.2 | — |
| Talc | — | 20.0 | — | 20.0 | — | — | 11.2 |
| Fumed Silica | — | — | 1.5 | 5.5 | — | — | 1.0 |

EXAMPLE 8

An aerosol antiperspirant composition according to the present invention is outlined under Table II.

TABLE II

| COMPONENT | WEIGHT % |
|---|---|
| Hexameric Cyclomethicone (DC 246) | 43.2 |
| ZAG | 6.7 |
| GE 1229 (25% elastomer in cyclomethicone) | 6.6 |
| Bentone 38CG ® | 3.5 |
| Isobutane (propellant) | 40.0 |

EXAMPLE 9

Another aerosol antiperspirant composition according to the present invention is outlined under Table III.

TABLE III

| COMPONENT | WEIGHT % |
|---|---|
| Aluminum Chlorhydrate | 12.0 |
| Isopropyl myristate | 7.1 |
| Hexameric Cyclomethicone (DC 246) | 7.0 |
| GE 1229 (25% elastomer in cyclomethicone) | 3.0 |
| Bentone 38 ® | 1.3 |
| Propylene Carbonate | 0.4 |
| Isobutane/Propane | 69.2 |

EXAMPLE 10

A solid stick antiperspirant composition according to the present invention is outlined under Table IV.

TABLE IV

| COMPONENT | WEIGHT % |
|---|---|
| Hexameric Cyclomethicone (DC 246) | 43.9 |
| Activated Aluminum Chlorhydrate | 22.6 |
| Talc | 20.0 |
| Stearyl Alcohol | 11.5 |
| Fragrance | 1.0 |
| GE 1229 (25% elastomer in DC 246) | 1.0 |

EXAMPLE 11

A gel formulation according to the present invention is outlined under Table V.

TABLE V

| COMPONENT | WEIGHT % |
|---|---|
| ZAG | 24.2 |
| Dipropylene Glycol | 18.0 |
| Dimethicone Copolyol (25% in DC 246) | 14.3 |
| Hexameric Cyclomethicone (DC 246) | 13.9 |
| GE 1229 (25% in DC 246) | 5.0 |
| Polysorbate 20 | 1.0 |
| Water | qs |

EXAMPLE 12

This Example presents comparative performance results with the selected cyclomethicones in an antiperspirant stick formulation. Six stick antiperspirants were formulated with various ratios of pentameric and hexameric cyclomethicones. The basic compositions are outlined in Table VI below.

TABLE VI

| COMPONENT | WEIGHT % |
|---|---|
| Cyclomethicone | 53.0 |
| Stearyl Alcohol | 14.0 |
| PEG-8-Distearate | 1.0 |
| Hydrogenated Castor Oil | 4.0 |
| Talc | 3.2 |
| ZAG | 24.0 |
| Fragrance | 0.8 |

The cyclomethicones were employed at different weight levels of pentameric (D5) and hexameric (D6) as follows.

| | |
|---|---|
| A | All D5 |
| B | 5.3:1 of D5:6 |
| C | 1.75:1 of D4:D5 |
| D | 1.5:1 of D5:D6 (representative of DC 345 Fluid) |
| E | 1:1 of D5:D6 |
| F | All D6 |

The test procedure for identifying whitening involved application of a layer of about 170 milligrams to black polyester fabric. Photos were taken at various times after application, including initial, 30, 60, 90, 120, 150, 180, 210, 240 and 270 minutes. Mean whiteness levels were calculated and are presented in Table VIII.

TABLE VII

| | MEAN WHITENESS VALUES | | | | | |
|---|---|---|---|---|---|---|
| TIME | A | B | C | D | E | F |
| 0 | 83.833 | 83.567 | 86.933 | 82.922 | 82.719 | 74.482 |
| 30 | 89.502 | 88.275 | 91.078 | 85.941 | 83.481 | 73.773 |
| 60 | 104.1 | 104.08 | 92.557 | 83.932 | 82.687 | 73.28 |
| 90 | 135.89 | 123.45 | 100.20 | 86.526 | 85.932 | 73.059 |
| 120 | 159.54 | 145.57 | 125.74 | 96.415 | 95.275 | 73.294 |
| 150 | 160.49 | 150.28 | 133.58 | 104.41 | 102.16 | 75.097 |
| 180 | 160.37 | 153.85 | 144.73 | 113.52 | 113.42 | 74.781 |
| 210 | 160.03 | 153.88 | 148.35 | 120.75 | 118.87 | 75.853 |
| 240 | 159.89 | 154.45 | 153.91 | 130.35 | 128.24 | 77.80 |
| 270 | 161.04 | 156.70 | 158.83 | 135.97 | 134.13 | 80.158 |
| Change from initial value | 77.207 | 73.133 | 71.897 | 53.048 | 51.411 | 5.676 |

Results of the study indicate that Sample F (all D6) was substantially better than the other samples at delaying the onset of any whitening. Sample E also had an effect, albeit much smaller. Samples A–D displayed various degrees of unacceptable whitening.

EXAMPLE 13

This Example presents comparative performance results with the selected cyclomethicones in an antiperspirant dry cream formulation. Six dry cream antiperspirants were formulated with various weight ratios of pentameric and hexameric cyclomethicones. The basic compositions are outlined in Table VIII below.

TABLE VIII

| COMPONENT | WEIGHT % |
| --- | --- |
| Cyclomethicone | 54.95 |
| Elastomer | 3.26 |
| Corn Starch | 15.10 |
| ZAG | 26.00 |
| Fragrance | 0.70 |

The cyclomethicones were employed at different weight levels of pentameric (D5) and hexameric (D6) as follows.

| | |
| --- | --- |
| G | All D5 |
| H | 0.2:1 of D5:D6 |
| I | 5.3:1 of D5:D6 |
| J | 1:1 of D5:D6 |
| K | 1.5:1 of D5:D6 (representative of DC 345 Fluid) |
| L | 1.75:1 of D5:D6 |

The test procedure for identifying whitening involved application of a layer of about 0.6 micron to black polyester fabric. Photos were taken at various times after application, including initial, 30, 60, 90, 120, 150, 180, 210, 240 and 270 minutes. Mean whiteness levels were calculated and are presented in Table IX.

TABLE IX

| | MEAN WHITENESS VALUES | | | | | |
| --- | --- | --- | --- | --- | --- | --- |
| TIME | G | H | I | J | K | L |
| 0 | 67.676 | 76.340 | 71.159 | 71.624 | 71.402 | 65.206 |
| 30 | 67.097 | 76.656 | 70.260 | 68.823 q | 70.012 | 64.344 |
| 60 | 66.118 | 76.042 | 68.693 | 67.357 | 68.415 | 63.037 |
| 90 | 66.288 | 72.559 | 66.217 | 63.883 | 64.828 | 60.235 |
| 120 | 74.933 | 72.251 | 70.125 | 64.769 | 65.264 | 61.030 |
| 150 | 83.659 | 71.547 | 75.124 | 65.010 | 66.118 | 62.256 |
| 180 | 95.328 | 71.040 | 81.239 | 66.474 | 68.152 | 64.680 |
| 210 | 107.677 | 70.083 | 88.771 | 68.918 | 72.083 | 67.025 |
| 240 | 117.483 | 69.469 | 96.833 | 71.575 | 75.921 | 71.109 |
| 270 | 128.203 | 69.307 | 106.750 | 75.024 | 80.987 | 75.814 |

TABLE IX-continued

| | MEAN WHITENESS VALUES | | | | | |
| --- | --- | --- | --- | --- | --- | --- |
| TIME | G | H | I | J | K | L |
| Change from initial value | 60.527 | −7.033 | 35.591 | 3.400 | 9.585 | 10.608 |

Sample G (all D5) whitened the quickest. Sample H (highest level of D6) whitened the least. Sample J (with equal amounts D5 and D6) was also relatively non-whitening, the change from its initial value being second smallest among the group of samples investigated.

The foregoing description and examples illustrate selected embodiments of the present invention. In light thereof variations and modifications will be suggested to one skilled in the art, all of which are within the spirit and purview of this invention.

What is claimed is:

1. An underarm composition comprising:
   (i) an underarm active present in an effective amount to inhibit odor or to reduce perspiration;
   (ii) from 5 to 80% by weight of the composition of hexameric cyclomethicone; and
   (iii) from 0 to 35% by weight based on total cyclomethicone present in the composition of tetrameric and pentameric cyclomethicone.

2. The composition according to claim 1 wherein the underarm active is present from 0.1 to 70% by weight of the composition.

3. The composition according to claim 1 wherein the underarm active is an astringent salt of a metal selected from the group consisting of aluminum, zirconium, zinc and mixtures thereof.

4. The composition according to claim 1 further comprising from 0.05 to 30% by weight of the composition of an organopolysiloxane elastomer.

5. The composition according to claim 4 wherein the organosiloxane elastomer is a crosslinked non-emulsifying siloxane elastomer.

6. The composition according to claim 5 wherein the elastomer is formed from a divinyl monomer reacting with Si—H linkages of a siloxane backbone.

7. The composition according to claim 1 wherein no more than 10% by weight based on total cyclomethicone present in the composition is of lower molecular weight cyclomethicone selected from the group consisting of tetrameric, pentameric and mixtures of these cyclomethicones.

8. The composition according to claim 1 wherein hexameric and combined tetrameric/pentameric cyclomethicone are present in relative weight ratios of at least about 1:1.

9. The composition according to claim 8 wherein the relative weight ratio is at least about 2:1.

* * * * *

UNITED STATES PATENT AND TRADEMARK OFFICE
CERTIFICATE OF CORRECTION

PATENT NO.    : 5,922,309
DATED         : July 13, 1999
INVENTOR(S)   : Brewster It is certified that error appears in the above-indentified patent and that said Letters Patent is hereby corrected as shown below:

TITLE PAGE:

In the Assignee Section change "Chesebrough-Pond's USA Co.,"

to read -- Chesebrough-Pond's USA Co., Division of Conopco, Inc. --

Signed and Sealed this

Twenty-third Day of November, 1999

Attest:

Q. TODD DICKINSON

Attesting Officer

Acting Commissioner of Patents and Trademarks